United States Patent [19]
Shaffer

[11] Patent Number: 5,714,564
[45] Date of Patent: Feb. 3, 1998

[54] LOW VISCOSITY POLYISOCYANATES PREPARED FROM MONOMERIC TRIISOCYANATES

[75] Inventor: Myron W. Shaffer, New Cumberland, W. Va.

[73] Assignee: Bayer Corporation, Pittsburgh, Pa.

[21] Appl. No.: 697,229

[22] Filed: Aug. 21, 1996

[51] Int. Cl.$^6$ .......................... C08G 18/79; C07D 251/34
[52] U.S. Cl. .................. 528/67; 252/182.2; 252/182.21; 252/182.22; 528/49; 528/73; 544/193; 544/222; 560/355; 564/44; 564/45
[58] Field of Search .......................... 252/182.2, 182.21, 252/182.22; 528/49, 67, 73; 544/193, 222; 560/355; 564/44, 45

[56] References Cited

U.S. PATENT DOCUMENTS

| | | | |
|---|---|---|---|
| 4,314,048 | 2/1982 | Doi et al. | 528/44 |
| 4,324,879 | 4/1982 | Bock et al. | 528/45 |
| 4,379,905 | 4/1983 | Stemmler et al. | 528/73 |
| 4,412,073 | 10/1983 | Robin | 544/193 |
| 4,801,663 | 1/1989 | Ueyanagi et al. | 525/528 |
| 5,124,427 | 6/1992 | Potter et al. | 528/67 |
| 5,208,334 | 5/1993 | Potter et al. | 544/193 |
| 5,235,018 | 8/1993 | Potter et al. | 528/49 |

OTHER PUBLICATIONS

Coating Systems Based onan Aliphatic Triisocyanate Derived from Triaminononane, Higginbottom et al, Third North American Research Conference on Organic Coating Science and Technology, Nov. 13–16, 1994.

*Primary Examiner*—Rabon Sergent
*Attorney, Agent, or Firm*—Joseph C. Gil; Thomas W. Roy

[57] ABSTRACT

The present invention is directed to a polyisocyanate containing a) polyisocyanates containing isocyanurate groups and corresponding to formula 1

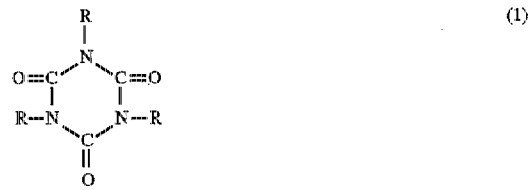

wherein

R represents the residue obtained by removing one of the isocyanate groups from 4-isocyanatomethyl-1,8-octamethylene diisocyanate, optionally in admixture with b) unreacted 4-isocyanatomethyl-1,8-octamethylene diisocyanate, c) higher homologs of the polyisocyanates set forth in formula 1 containing more than one isocyanurate group and d) a polyisocyanate containing allophanate groups.

The present invention also relates to the use of these polyisocyanate mixtures, optionally in blocked form, as an isocyanate component in one- or two-component coating compositions.

19 Claims, No Drawings

LOW VISCOSITY POLYISOCYANATES PREPARED FROM MONOMERIC TRIISOCYANATES

BACKGROUND OF THE INVENTION

1. Field of the Invention

The present invention is directed to low viscosity polyisocyanates containing isocyanurate groups and optionally allophanate groups and prepared from 4-isocyanatomethyl-1,8-octamethylene diisocyanate, and to their use in one- and two-component compositions for the production of polyisocyanate addition products.

2. Description of the Prior Art

Polyisocyanates containing isocyanurate groups are known and disclosed in U.S. Pat. Nos. 4,324,879, 4,379,905, 4,412,073 and 4,801,663. Polyisocyanates containing isocyanurate groups and allophanate groups are known and disclosed in U.S. Pat. Nos. 5,124,427, 5,208,334 and 5,235,018. Both of these types of polyisocyanates are prepared by the catalytic trimerization and optionally allophanatization of a portion of the isocyanate groups of monomeric diisocyanates followed by distillation to remove unreacted diisocyanate monomers. The reaction product not only contains the trifunctional monotrimer, i.e., an isocyanurate group-containing polyisocyanate prepared from three moles of diisocyanate, but also higher homologs containing two or more isocyanurate rings.

During the trimerization reaction the monotrimer is initially formed; however, as the reaction proceeds and the percentage of the starting monomer decreases, higher homologs containing two or more isocyanurate rings are formed. While these higher homologs have desirably higher functionalities, they also have undesirably higher viscosities. Because the market is constantly striving for products with low viscosities, it is necessary to terminate the trimerization reaction at a very early stage to obtain these products. For this reason it is difficult to obtain products with higher functionalities, even though such products (purely from a functionality standpoint) would be desirable for many applications.

Accordingly, it is an object of the present invention to provide polyisocyanates that have high functionalities and low viscosities and also may be prepared without the necessity of removing unreacted starting material.

Surprisingly, this objective can be achieved by preparing the isocyanurate group-containing polyisocyanates from 4-isocyanatomethyl-1,8-octamethylene diisocyanate or mixtures containing this polyisocyanate. The fact that these products have high functionalities, low viscosities and do not contain gel particles is surprising because due to the fact that the starting monomer is a triisocyanate, it would be expected that cross-linked gel particles would form and that greater amounts of the higher homologs would form resulting in higher viscosities.

4-isocyanatomethyl-1,8-octamethylene diisocyanate has been disclosed in U.S. Pat. No. 4,314,048 and in the article entitled "Coating Systems Based on an Aliphatic Triisocyanate Derived From Triaminononane", Higginbottom et al, Third North American Research Conference on Organic Coatings Science and Technology, 1994. However, both of these references promote the triisocyanate itself as a substitute for polyisocyanate derivatives, in particular isocyanurate group-containing polyisocyanates prepared from 1,6-hexamethylene diisocyanate, thus eliminating the need for preparing such adducts.

SUMMARY OF THE INVENTION

The present invention is directed to a polyisocyanate containing a) polyisocyanates containing isocyanurate groups and corresponding to formula 1

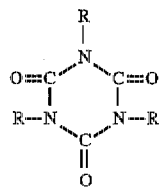

(1)

wherein
R represents the residue obtained by removing one of the isocyanate groups from 4-isocyanatomethyl-1,8-octamethylene diisocyanate, optionally in admixture with b) unreacted 4-isocyanatomethyl-1,8-octamethylene diisocyanate, c) higher homologs of the polyisocyanates set forth in formula 1 containing more than one isocyanurate group and d) a polyisocyanate containing allophanate groups and corresponding to formula 2

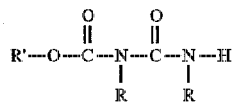

(2)

wherein
R' represents the residue obtained by removing the hydroxy group from a monoalcohol having a molecular weight of up to 2500.

The present invention also relates to the use of these polyisocyanate mixtures, optionally in blocked form, as an isocyanate component in one- or two-component coating compositions.

DETAILED DESCRIPTION OF THE INVENTION

In accordance with the present invention polyisocyanates a) containing isocyanurate groups are present in an amount of preferably 5 to 40% by weight, more preferably 10 to 25% by weight; unreacted monomer b) is present in an amount of preferably 20 to 90% by weight, more preferably 40 to 60% by weight and higher homologs c) are present in an amount of preferably 5 to 70% by weight, more preferably 20 to 60% by weight. All of these percentages are based on the total weight of components a), b) and c). Polyisocyanates d) containing allophanate groups are present, if at all, in an amount of up to 25% by weight, preferably 2 to 25% by weight, more preferably 5 to 20% by weight, based on the total weight of components a), b) and c).

The polyisocyanates according to the invention are prepared from a) 30 to 100%, preferably 60 to 100%, more preferably 90 to 100% and most preferably 100% by weight of 4-isocyanatomethyl-1,8-octamethylene diisocyanate (NTI) and b) 0 to 70% by weight, preferably 0 to 40% by weight, more preferably 0 to 10% by weight and most preferably 0% by weight of one more organic diisocyanates corresponding to the formula

wherein R" represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms and a divalent aromatic hydrocarbon group having 6 to 15 carbon atoms.

Examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethylcyclo-hexane (isophorone diisocyanate or IPDI), bis-(4-isocyanatocyclohexyl)-methane, 2,4'-diisocyanato-dicyclohexyl methane, 1,3- and 1,4-bis-(isocyanatomethyl)-cyclohexane, bis-(4-isocyanato-3-methyl-cyclohexyl)-methane, xylylene diisocyanate, α,α, α',α'-tetramethyl-1,3- and/or -1,4-xylylene diisocyanate, 1-isocyanato-1-methyl-4(3)-isocyanato-methyl cyclohexane, and 2,4- and/or 2,6-hexahydrotoluylene diisocyanate, 1,3- and/or 1,4-phenylene diisocyanate, 2,4- and/or 2,6-toluylene diisocyanate, 2,4- and/or 4,4'-diphenylmethane diisocyanate, 1,5-diisocyanato naphthalene and mixtures thereof.

Preferred organic diisocyanates include 1,6-hexamethylene diisocyanate, isophorone diisocyanate, bis-(4-isocyanatocyclohexyl)-methane, 2,4- and/or 2,6-toluylene diisocyanate and 2,4- and/or 4,4'-diphenylmethane diisocyanate.

Suitable methods and catalysts for the preparation of polyisocyanates containing isocyanurate groups are disclosed in U.S. Pat. Nos. 4,324,879 and 5,157,074, the disclosure of which are herein incorporated by reference. Suitable methods and catalysts for the preparation of polyisocyanates containing isocyanurate groups and allophanate groups are known and described in U.S. Pat. Nos. 5,124,427, 5,208,334, 5,235,018 and 5,444,146, the disclosures of which are herein incorporated by reference.

The trimerization of the starting isocyanate or isocyanate mixture may be carried out in the absence or in the presence of solvents which are inert to isocyanate groups. Depending on the area of application of the products according to the invention, low- to medium-boiling solvents or high-boiling solvents can be used. Suitable solvents include esters such as ethyl acetate or butyl acetate; ketones such as acetone or butanone; aromatic compounds such as toluene or xylene; halogenated hydrocarbons such as methylene chloride and trichloroethylene; ethers such as diisopropylether; and alkanes such as cyclohexane, petroleum ether or ligroin.

In accordance with an optional embodiment of the present invention urethane groups and subsequently allophanate groups are incorporated into the polyisocyanates by the use of aliphatic, cycloaliphatic, araliphatic or aromatic monoalcohols, i.e., alcohols in which the hydroxyl group is attached to aliphatic, cycloaliphatic, araliphatic or aromatic group. The monoalcohols may be linear, branched or cyclic, contain at least one carbon atom and have a molecular weight of up to 2500. The monoalcohols may optionally contain other hetero atoms in the form of, e.g., ether groups. The molar ratio of monoalcohol to isocyanate starting material is about 0.005:1 to 0.60:1, preferably about 0.01:1 to 0.60:1, more preferably about 0.02:1 to 0.50:1 and most preferably about 0.05:1 to 0.50:1.

Preferred monoalcohols are hydrocarbon monoalcohols. The hydrocarbon monoalcohols preferably contain 1 to 36, more preferably 1 to 20 and most preferably 1 to 8 carbon atoms. Examples of suitable monoalcohols include methanol, ethanol, n-propanol, isopropanol, n-butanol, isobutanol and tert. butanol, n-pentanol, 2-hydroxy pentane, 3-hydroxy pentane, the isomeric methyl butyl alcohols, the isomeric dimethyl propyl alcohols, neopentyl alcohol, n-hexanol, n-heptanol, n-octanol, n-nonanol, 2-ethyl hexanol, trimethyl hexanol, cyclohexanol, benzyl alcohol, phenol, the cresols, the xylenols, the trimethylphenols, decanol, dodecanol, tetradecanol, hexadecanol, octadecanol, 2,6,8-trimethylnonanol, 2-t-butyl-cyclohexanol, 4-cyclohexyl-1-butanol, 2,4,6,-trimethyl benzyl alcohol, branched chain primary alcohols and mixtures thereof (which are available from Henkel under to Standamul trademark) and mixtures of linear primary alcohols (which are available from Shell under the Neodol trademark).

Other examples of suitable monoalcohols are set forth in U.S. Pat. Nos. 5,124,427, 5,208,334 and 5,235,018, the disclosures of which have previously been incorporated by reference. It is also possible in accordance with the present invention to use mixtures of the previously described monoalcohols.

The reaction temperature for isocyanurate and optionally allophanate formation in accordance with the present invention is about 40° to 180° C., preferably about 50° to 150° C. and more preferably about 60° to 120° C.

Processes for the preparation of polyisocyanates containing isocyanurate groups or polyisocyanates containing isocyanurate and allophanate groups are set forth in the U.S. patents previously incorporated by reference. The progress of the reaction is followed by determining the NCO content by a suitable method such as titration, refractive index or IR analysis. The reaction may be terminated at the desired degree of trimerization. The trimerization reaction is generally terminated when 4 to 33%, preferably 10 to 30%, and more preferably 15 to 25%, of the isocyanate groups have reacted. This corresponds on a theoretical basis to reacting one isocyanate group from 12 to 100%, preferably 30 to 90% and more preferably 45 to 75%, of the starting isocyanate monomer. In actual practice before one isocyanate group is reacted from each molecule of starting isocyanate, the isocyanate groups present in the polyisocyanates containing isocyanurate groups begin to react resulting in the formation of polyisocyanates containing more than one isocyanurate group.

By terminating the reaction at higher NCO contents, lower viscosity polyisocyanates are obtained. To the contrary when the reaction is terminated at lower NCO contents, higher viscosity polyisocyanates are obtained due to the formation of higher molecular weight polyisocyanates containing two or more isocyanurate groups and optionally other high molecular weight polyisocyanates.

The termination of the trimerization reaction can take place, for example, by the addition of a catalyst, poison of the type named by way of example in the previously disclosed U.S. patents. For example, when using basic catalysts the reaction may be terminated by the addition of a quantity, which is at least equivalent to the catalyst quantity, of an acid. When using heat-labile catalysts it is possible, though not preferred, to dispense with the addition of a catalyst poison since these catalysts decompose during the course of the reaction.

When preparing the known polyisocyanates containing isocyanurate groups from volatile diisocyanates, such as 1,6-hexamethylene diisocyanate, toluene diisocyanate or isophorone diisocyanate, it is necessary to remove unreacted starting diisocyanate from the final product, e.g., by distillation, to a content of less than 2%, preferably less than 1% by weight, based on the weight of the polyisocyanate. However, when preparing the polyisocyanates according to the present invention it is possible, but not necessary, to remove 4-isocyanatomethyl-1,8-octamethylene diisocyanate because this triisocyanate is not as volatile as the diisocyanates conventionally used. In addition, because of its functionality, the presence of this triisocyanate does not reduce the crosslinking ability of the final product.

The products according to the invention are liquids having a viscosity of 10 to 10,000 mPa•s, preferably 50 to 3000 mPa•s and more preferably 50 to 1000 mPa•s. The viscosity of the product is determined by the degree of trimerization (which corresponds to the formation of higher functional, higher viscosity homologs) and the amount of unreacted monomer present in the product. Lower viscosities may be obtained by terminating the reaction at a lower degree of trimerization and/or by not removing unreacted starting material.

The polyisocyanate mixtures according to the invention have a minimum average functionality of 3, preferably 3.2 and more preferably 3.5 and a maximum average functionality of 8, preferably 6 and more preferably 5; have an isocyanate content of preferably 33 to 48% by weight, more preferably 35 to 45% by weight, and most preferably 37 to 43% by weight, based on polyisocyanate solids; and are almost colorless, i.e., they have a yellowness index as measured on the APHA color scale of 10 to 150, preferably 10 to 100 and more preferably 10 to 50.

The products according to the present invention are polyisocyanates containing isocyanurate groups and optionally allophanate groups. The products may also contain residual urethane groups which have not been converted to allophanate groups depending upon the temperature maintained during the reaction and the degree of isocyanate group consumption. However, the content of urethane groups (calculated as NHCOO, MW 59) should be less than 10% by weight, preferably less than 5% by weight and more preferably less than 2%, based on the solids content of the polyisocyanate mixture. When preparing polyisocyanates containing both isocyanurate and allophanate groups and, the ratio of isocyanurate groups to allophanate groups in the polyisocyanates according to the invention is preferably about 10:1 to 1:10, more preferably about 5:1 to 1:7. These values may be determined spectroscopically or by gel permeation chromatography (GPC) using a standard.

The products according to the invention are valuable starting materials for use in two-component coating compositions for the production of polyisocyanate polyaddition products. The polyisocyanate component is used in combination with compounds containing at least two isocyanate-reactive groups, such as hydroxyl groups and/or amino groups, preferably hydroxyl groups.

Preferred reaction partners for the products according to the invention, which may optionally be present in blocked form, are the polyhydroxy polyesters, polyhydroxy polyethers, polyhydroxy polyacrylates, polyhydroxy polylactones, polyhydroxy polyurethanes, polyhydroxy polyepoxides and optionally low molecular weight, polyhydric alcohols known from polyurethane coatings technology. Polyamines, particularly in blocked form, for example as polyketimines, oxazolidines or polyaldimines are also suitable reaction partners for the products according to the invention. Also suitable are polyaspartic acid derivatives (aspartates) containing secondary amino groups, which also function as reactive diluents.

To prepare the coating compositions the amount of the polyisocyanate component and the isocyanate reactive component are selected to provide equivalent ratios of isocyanate groups (whether present in blocked or unblocked form) to isocyanate-reactive groups of about 0.5 to 20, preferably 0.8 to 3 and more preferably about 0.9 to 1.5.

To accelerate hardening, the coating compositions may contain known polyurethane catalysts, e.g., tertiary amines such as triethylamine, pyridine, methyl pyridine, benzyl dimethylamine, N,N-dimethylamino cyclohexane, N-methyl-piperidine, pentamethyl diethylene triamine, 1,4-diazabicyclo[2,2,2]-octane and N,N'-dimethyl piperazine; or metal salts such as iron(III)-chloride, zinc chloride, zinc-2-ethyl capmate, tin(II)-ethyl caproate, dibutyltin(IV)-dilaurate and molybdenum glycolate.

The products according to the invention are also valuable starting materials for two-component polyurethane stoving enamels in which the isocyanate groups are used in a form blocked by known blocking agents. The blocking reaction is carried out in known manner by reacting the isocyanate groups with suitable blocking agents, preferably at an elevated temperature (e.g. about 40° to 160° C.), and optionally in the presence of a suitable catalyst, for example, the previously described tertiary amines or metal salts.

Suitable blocking agents include monophenols such as phenol, the cresols, the trimethylphenols and the tert. butyl phenols; tertiary alcohols such as tert. butanol, tert. amyl alcohol and dimethylphenyl carbinol; compounds which easily form enols such as acetoacetic ester, acetyl acetone and malonic acid derivatives, e.g. malonic acid diethylester; secondary aromatic amines such as N-methyl aniline, the N-methyl toluidine, N-phenyl toluidine and N-phenyl xylidine; imides such as succinimide; lactams such as $\epsilon$-caprolactam and $\delta$-valerolactam; oximes such as butanone oxime, methyl amyl ketoxime and cyclohexanone oxime; mercaptans such as methyl mercaptan, ethyl mercaptan, butyl mercaptan, 2-mercaptobenzthiazole, $\alpha$-naphthyl mercaptan and dodecyl mercaptan; and triazoles such as 1H-1,2,4-triazole.

The coating compositions may also contain other additives such as pigments, dyes, fillers, levelling agents and solvents. The coating compositions may be applied to the substrate to be coated in solution or from the melt by conventional methods such as painting, rolling, pouring or spraying.

The coating compositions containing the polyisocyanates according to the invention provide coatings which have improved dry times, adhere surprisingly well to a metallic base, and are particularly light-fast, color-stable in the presence of heat and very resistant to abrasion. Furthermore, they are characterized by high hardness, elasticity, very good resistance to chemicals, high gloss, good weather resistance, good environmental etch resistance and good pigmenting qualities. The polyisocyanates according to the invention also possess good compatibility with highly branched polyester resins.

The invention is further illustrated, but is not intended to be limited by the following examples in which all parts and percentages are by weight unless otherwise specified.

EXAMPLES

In the following examples the catalyst solution was prepared by dissolving 1.0 g of trimethylbenzyl ammonium hydroxide, which is present as a 40% in methanol, into 7.0 g of propylene glycol monoethyl ether acetate (PMA). The stopper solution was prepared by dissolving 1.0 g of di(2-ethylhexyl)phosphoric acid into 3.0 g of 4-isocyanatomethyl-1,8-octamethylene diisocyanate (NTI).

Example 1

Preparation of a Polyisocyanate According to the Invention 100 g of NTI were placed into a three-neck round bottom flask equipped with a mechanical stirrer, addition funnel, nitrogen sparge tube and a thermocouple. The triisocyanate was sparged for 2 hours with nitrogen at 90° C. while stirring. A total of 1.0 g of catalyst solution was added dropwise over 40 minutes, while maintaining the temperature at 90° C. The reaction was stopped at an NCO content of 42.0% (48% theoretical conversion) by adding 0.4 g of stopper solution. The resulting product was a clear, light yellow liquid, which did not contain gel particles and had the following properties:
functionality: 3.69
viscosity: 80 mPa•s (25° C., #3 spindle at 60 rpm).

Example 2

Preparation of a Polyisocyanate According to the Invention 100 g of NTI were placed into a three-neck round bottom flask equipped with a mechanical stirrer, addition funnel, nitrogen sparge tube and a thermocouple. The triisocyanate was sparged for 2 hours with nitrogen at 90° C. while stirring. A total of 1.2 g of catalyst solution was added dropwise over 20 minutes, while maintaining the temperature at 90° C. The reaction was stopped at an NCO content of 40.4% (60% theoretical conversion) by adding 0.5 g of stopper solution. The resulting product was a clear, light yellow liquid, which did not contain gel particles and had the following properties:
functionality: 4.08
viscosity: 260 mPa•s (25° C., #3 spindle at 60 rpm).

Example 3

Preparation of a Polyisocyanate According to the Invention 100 g of NTI were placed into a three-neck round bottom flask equipped with a mechanical stirrer, addition funnel, nitrogen sparge tube and a thermocouple. The triisocyanate was sparged for 2 hours with nitrogen at 90° C. while stirring. A total of 0.95 g of catalyst solution was added dropwise over 40 minutes, while maintaining the temperature at 90° C. The reaction was stopped at an NCO content of 34.9 % (90% theoretical conversion) by adding 0.4 g of stopper solution. The resulting product was a clear, light yellow liquid, which did not contain gel particles and had the following properties:
functionality: 4.93
viscosity: 5500 mPa•s (25° C., #3 spindle at 60 rpm)

Example 4

Comparison 250 g of hexamethylene diisocyanate were placed into a three-neck round bottom flask equipped with a mechanical stirrer, addition funnel, nitrogen sparge tube and a thermocouple. The diisocyanate was sparged for 1.5 hours with nitrogen at 90° C. while stirring. A total of 1.0 g of catalyst solution was added dropwise over 2 minutes, while maintaining the temperature at 90° C. The reaction was stopped at 37.9% NCO (48.4% theoretical conversion) by adding 0.4 g of stopper solution. The resulting product was a clear, light yellow liquid having the following properties:
functionality (unstripped): 2.37
viscosity (unstripped): 13 mPa•s (25° C., #2 spindle at 100 rpm).

When all of the monomer is removed from this product, it has the following properties:
functionality (stripped): 3.53

Example 5

Comparison

An isocyanurate group-containing polyisocyanate (available from Bayer Corporation as Desmodur N 3300) prepared from 1,6-hexamethylene diisocyanate and having an isocyanate content of 21.6%, a content of monomeric diisocyanate of <0.2% and the following properties:
functionality (stripped): 3.57
viscosity (stripped): 3000 mPa•s (25° C.)

Example 6

Comparison 250 g of hexamethylene diisocyanate were placed into a three-neck round bottom flask equipped with a mechanical stirrer, addition funnel, nitrogen sparge tube and a thermocouple. The diisocyanate was sparged for 1.5 hours with nitrogen at 90° C. while stirring. A total of 1.0 g of catalyst solution was added dropwise over 2 minutes, while maintaining the temperature at 90° C. The reaction was stopped at an NCO content of 34.28% NCO (63% theoretical conversion) by adding 0.4 g of stopper solution. The resulting product was a clear, light yellow liquid having the following properties:
functionality (unstripped): 2.57
viscosity (unstripped): 38 mPa•s (25° C., #2 spindle at 100 rpm)

When all of the monomer was removed from this product, it had the following properties:
functionality (stripped): 3.78
viscosity (stripped): 12,320 mPa•s (25° C., #3 spindle at 60 rpm)

Example 7

Comparison 250 g of hexamethylene diisocyanate were placed into a three-neck round bottom flask equipped with a mechanical stirrer, addition funnel, nitrogen sparge tube and a thermocouple. The diisocyanate was sparged for 1.5 hours with nitrogen at 90° C. while stirring. A total of 1.0 g of catalyst solution was added dropwise over 2 minutes, while maintaining the temperature at 90° C. The reaction was stopped at 25.45% NCO (98% theoretical conversion) by adding 0.4 g of stopper solution. The resulting product was a clear, light yellow liquid having the following properties:
functionality (unstripped): 3.39
viscosity (unstripped): 1950 mPa•s (25° C., #2 spindle at 30 rpm)

When all of the monomer is removed from this product, it has the following properties:
functionality (stripped): 4.71

The following table summarizes the data set forth in the preceding examples:

| Example | % Conversion | Functionality | | Viscosity (mPa.s) | |
| --- | --- | --- | --- | --- | --- |
| | | Unstripped | Stripped | Unstripped | Stripped |
| 1 | 48 | 3.69 | — | 80 | — |
| 2 | 60 | 4.08 | — | 260 | — |
| 3 | 90 | 4.93 | — | 5500 | — |
| 4 (comp) | 48 | 2.37 | 3.53 | 13 | — |
| 5 (comp) | — | — | 3.57 | — | 3000 |
| 6 (comp) | 60 | 2.57 | 3.78 | 38 | 12,320 |
| 7 (comp) | 98 | 3.39 | 4.71 | 1950 | — |

The following is apparent from the data set forth in the table:

1) When products having similar viscosities are compared, e.g., the polyisocyanates from example 1 and comparison example 6 (unstripped), the functionalities of the comparison polyisocyanates are substantially less than the functionalities of the polyisocyanate according to the invention.

2) When products having similar functionalities are compared, the polyisocyanates according to the invention have substantially lower viscosities than the comparison polyisocyanates and do not contain gel particles. For example, the polyisocyanate from example 2, which has a functionality of 4.1, has a viscosity of 260. To the contrary the polyisocyanates from comparison examples 5 and 6 (stripped), even though they have lower functionalities of 3.57 and 3.78, have substantially higher viscosities of 3000 and 12,320, respectively. It is also apparent from this data that small changes in functionality cause significant increases in viscosity.

3) As the percent conversion increases for both the polyisocyanates according to the invention and for the comparison polyisocyanates, the functionality and viscosity also increase. Therefore, even though the viscosity was not determined for comparison example 7 (stripped), the viscosity of this polyisocyanate (due to its higher functionality and percent conversion) would be higher than for the polyisocyanate obtained in comparison example 6 (stripped) and this value is already higher than that obtained in example 3 according to the invention.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyisocyanate comprising
a) a polyisocyanate containing an isocyanurate group and corresponding to formula 1

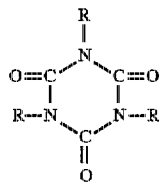
(1)

wherein
R represents the residue obtained by removing one of the isocyanate groups from 4-isocyanatomethyl-1,8-octamethylene diisocyanate,
optionally in admixture with one or more of the following:
b) unreacted 4-isocyanatomethyl-1,8-octamethylene diisocyanate,
c) higher homologs of the polyisocyanates set forth in formula 1 containing more than one isocyanurate group and
d) a polyisocyanate containing allophanate groups and corresponding to formula 2

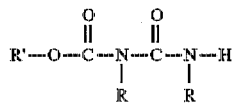
(2)

wherein
R' represents the residue obtained by removing the hydroxy group from a monoalcohol having a molecular weight of up to 2500.

2. The polyisocyanate of claim 1 wherein component a) is present in an amount of 5 to 40% by weight, component b) is present in an amount of 20 to 90% by weight and component c) is present in an amount of 5 to 70% by weight, wherein the preceding percentages are based on total weight of components a), b) and c).

3. The polyisocyanate of claim 1 wherein component a) is present in an amount of 10 to 25% by weight, component b) is present in an amount of 40 to 60% by weight and component c) is present in an amount of 20 to 60% by weight, wherein the preceding percentages are based on total weight of components a), b) and c).

4. The polyisocyanate of claim 1 which has an average functionality of 3 to 6.

5. The polyisocyanate of claim 2 which has an average functionality of 3 to 6.

6. The polyisocyanate of claim 3 which has an average functionality of 3 to 6.

7. A polyisocyanate comprising
a) a polyisocyanate containing an isocyanurate group and corresponding to formula 1

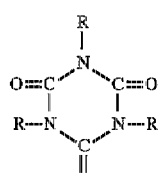
(1)

wherein
R represents the residue obtained by removing one of the isocyanate groups from 4-isocyanatomethyl-1,8-octamethylene diisocyanate,
b) optionally unreacted 4-isocyanatomethyl-1,8-octamethylene diisocyanate,
c) optionally higher homologs of the polyisocyanates set forth in formula 1 containing more than one isocyanurate group and
d) a polyisocyanate containing allophanate groups and corresponding to formula 2

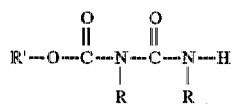
(2)

wherein
R' represents the residue obtained by removing the hydroxy group from
a monoalcohol having a molecular weight of up to 2500.

8. The polyisocyanate of claim 7 wherein component d) is present in an amount of 2 to 25% by weight, based on the total weight of components a), b) and c).

9. The polyisocyanate of claim 7 wherein component a) is present in an amount of 5 to 40% by weight, component b) is present in an amount of 20 to 90% by weight, component c) is present in an amount of 5 to 70% by weight and component d) is present in an amount of 2 to 25% by weight, wherein the preceding percentages are based on the total weight of components a), b) and c).

10. The polyisocyanate of claim 7 wherein component a) is present in an amount of 10 to 25% by weight, component b) is present in an amount of 40 to 60% by weight, component c) is present in an amount of 20 to 60% by weight and component d) is present in an amount of 5 to 20% by weight, wherein the preceding percentages are based on total weight of components a), b) and c).

11. The polyisocyanate of claim 7 wherein R' represents the residue obtained by removing the hydroxy group from a monoalcohol containing 1 to 20 carbon atoms.

12. The polyisocyanate of claim 8 wherein R' represents the residue obtained by removing the hydroxy group from a monoalcohol containing 1 to 20 carbon atoms.

13. The polyisocyanate of claim 9 wherein R' represents the residue obtained by removing the hydroxy group from a monoalcohol containing 1 to 20 carbon atoms.

14. The polyisocyanate of claim 10 wherein R' represents the residue obtained by removing the hydroxy group from a monoalcohol containing 1 to 20 carbon atoms.

15. The polyisocyanate of claim 7 wherein R' represents the residue obtained by removing the hydroxy group from a monoalcohol containing 1 to 8 carbon atoms.

16. The polyisocyanate of claim 8 wherein R' represents the residue obtained by removing the hydroxy group from a monoalcohol containing 1 to 8 carbon atoms.

17. The polyisocyanate of claim 9 wherein R' represents the residue obtained by removing the hydroxy group from a monoalcohol containing 1 to 8 carbon atoms.

18. The polyisocyanate of claim 10 wherein R' represents the residue obtained by removing the hydroxy group from a monoalcohol containing 1 to 8 carbon atoms.

19. A one- or two-component coating composition comprising the polyisocyanate of claim 1 and a compound containing isocyanate-reactive groups.

* * * * *